United States Patent [19]
Grozinger

[11] Patent Number: 6,136,982
[45] Date of Patent: Oct. 24, 2000

[54] SYNTHESIS OF 3-AMINO-2-CHLORO-4-METHYLPYRIDINE FROM ACETONE AND ETHYL CYANOACETATE

[75] Inventor: Karl Grozinger, Ridgefield, Conn.

[73] Assignee: Boehringer Ingelheim Pharmaceuticals, Inc., Ridgefield, Conn.

[21] Appl. No.: 09/478,588

[22] Filed: Jan. 6, 2000

Related U.S. Application Data

[60] Provisional application No. 60/116,703, Jan. 22, 1999.
[51] Int. Cl.[7] .................................................. C07D 213/72
[52] U.S. Cl. ............................................................... 546/250
[58] Field of Search ............................................... 546/250

[56] References Cited

U.S. PATENT DOCUMENTS 5,654,429  8/1997  Nummy .
5,686,618  11/1997  Schneider .

OTHER PUBLICATIONS

Bagley et al. Synthesis and alpha–2–Adrenergic Activities of Imidazole and Imidazolidine Analogues: In Vitro and In Vivo Selectivity, Med. Chem. Res. 4: 346–364, 1994.

Norman et al. Structural Elucidation of an Oxazolo[5,4–b] pyridine: an Alternative Cyclization Product Related to Nevirapine, J. Heterocyclic Chem., 30, 771–779, 1993.

Klunder et al. Novel Non–Nucleoside Inhibitors of HIV–1 Reverse Transcriptase. 2. Tricyclic Pyridobenzoxazepinones and Dibenzoxazepinones J. Med. Chem. 35:1887–1897, 1992.

Chapman, et al; J. Chem. Soc. Perkin Trans. I, 2398–2404; 1980.

Grozinger, et al; J. Heterocyclic Chem., 32, 259; 1995.

Zhang, et al; Tetrahedron 51 (48); 13177–13184; 1995.

Hargrave, et al; J. Heterocyclic Chem., 34, 223; 1991.

*Primary Examiner*—Joseph McKane
*Assistant Examiner*—Sonya N. Wright
*Attorney, Agent, or Firm*—Robert P. Raymond; Alan R. Stempel; Mary-Ellen M. Devlin

[57] ABSTRACT

A method for making 3-amino-2-chloro-4-methylpyridine from acetone and ethyl cyanoacetate, as depicted in the following reaction scheme.

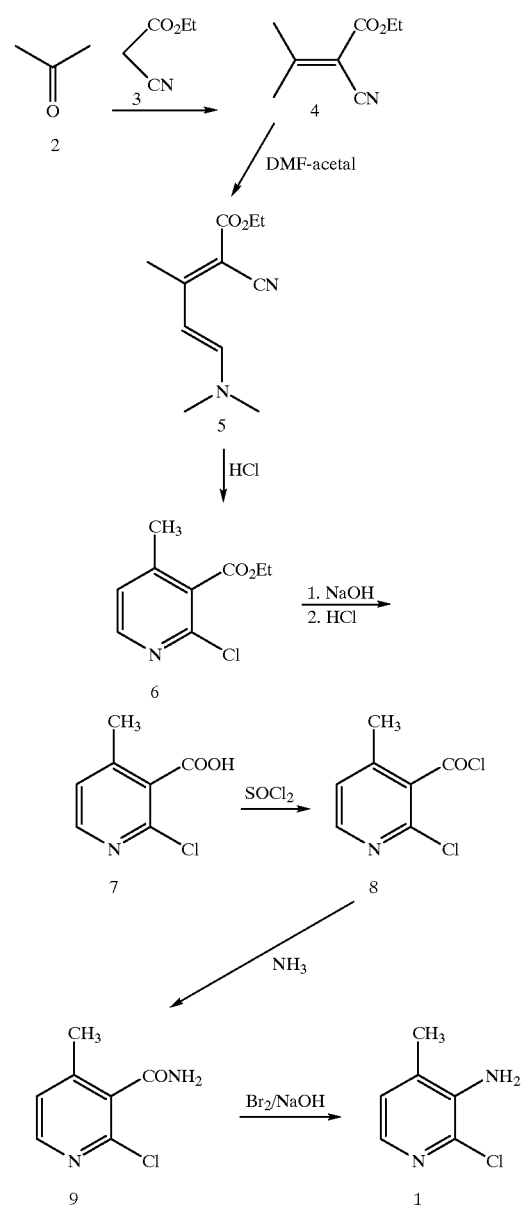

1 Claim, No Drawings

SYNTHESIS OF 3-AMINO-2-CHLORO-4-METHYLPYRIDINE FROM ACETONE AND ETHYL CYANOACETATE

RELATED APPLICATIONS

The benefit of prior provisional application Serial No. 60/116,703, filed on Jan. 22, 1999, is hereby claimed.

BACKGROUND OF THE INVENTION

1. Field of the Invention

The present invention relates to a regioselective method for making 3-amino-2-chloro-4-methylpyridine from acetone and ethyl cyanoacetate.

2. Description of Related Art Including Information Disclosed Under 37 CFR 1.97 and 1.98

As described in U.S. Pat. No. 5,366,972, the compound 3-amino-2-chloro-4-methylpyridine is useful as an intermediate material for the synthesis of 11-cyclopropyl-5,11-dihydro-4-methyl-6H-dipyrido[3,2-b:2',3'-e][1,4]diazepin-6-one, an HIV reverse transcriptase inhibitor useful for the treatment of HIV-1, known as nevirapine.

There are several known methods for the synthesis of 3-amino-2-chloro-4-methylpyridine. An early synthesis, beginning from 2-chloro-4-methyl-3-nitropyridine, has been described by Chapman et al. (J. Chem. Soc. Perkin Trans. I, 2398–2404 (1980)). As reported by Grozinger et al. (J. Heterocyclic Chem., 32, 259 (1995)), the compound has been synthesized in small laboratory batches by nitrating the readily available 2-amino-4-picoline or 2-hydroxy-4-picoline. This procedure suffers from non-selective nitration at positions 3 and 5, as well as thermo-chemical hazards and potential for "run-away" when carried out in large. The drawbacks of the nitration-based process lead to the development of two related synthetic routes starting from ethylacetoacetate and cyanacetamide, as described in U.S. Pat. Nos. 5,668,287 and 5,200,522. Both of the latter two synthetic routes require the dichlorination of the intermediate 2,6-dihydroxy-4-methyl-3-pyridinecarbonitrile, at positions 2 and 6, subsequent de-chlorination and finally selective re-chlorination at position 2. The di-chlorination and dehalogenation, as well as the selective monochlorination at position 2 require special manufacturing equipment that is expensive and which may not be readily available. Yet another synthesis, comprising the steps chlorination of ethyl cyanoacetate, Michael addition with crotonaldehyde, cyclization, conversion to the amide and finally reduction to the amine has been described by Zhang et al. (Tetrahedron 51(48), 13177–13184 (1995)), who report that while the desired product was obtained, the Michael addition was slow and the cyclization low-yielding. Schneider (U.S. Pat. No. 5,686,618) has provided a synthesis involving the reduction of 2,6-dichloro-3-amino-4-methylpyridine and monochlorination using $H_2O_2$ in HCl without isolation of the intermediate 3-amino-4-picoline. A synthesis beginning with 2-chloro-3-aminopyridine has been disclosed by Nummy (U.S. Pat. No. 5,654,429).

SUMMARY OF THE INVENTION

The present invention provides an improved method for making 3-amino-2-chloro-4-methylpyridine which comprises the steps depicted below in the following reaction scheme.

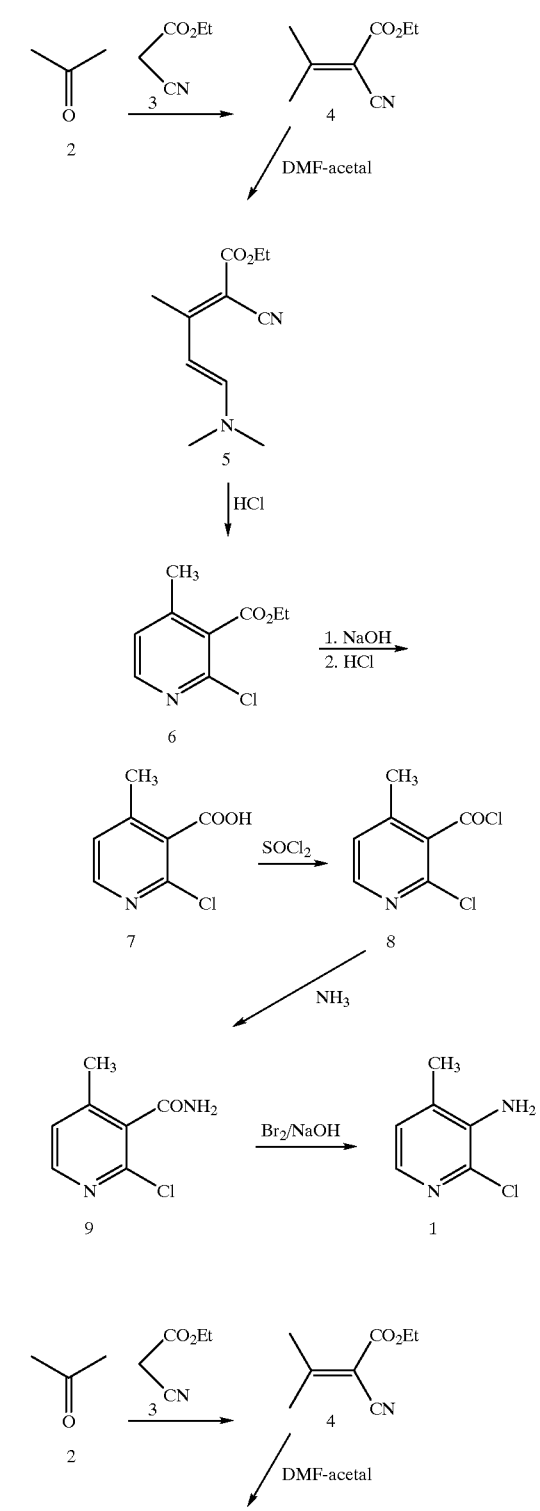

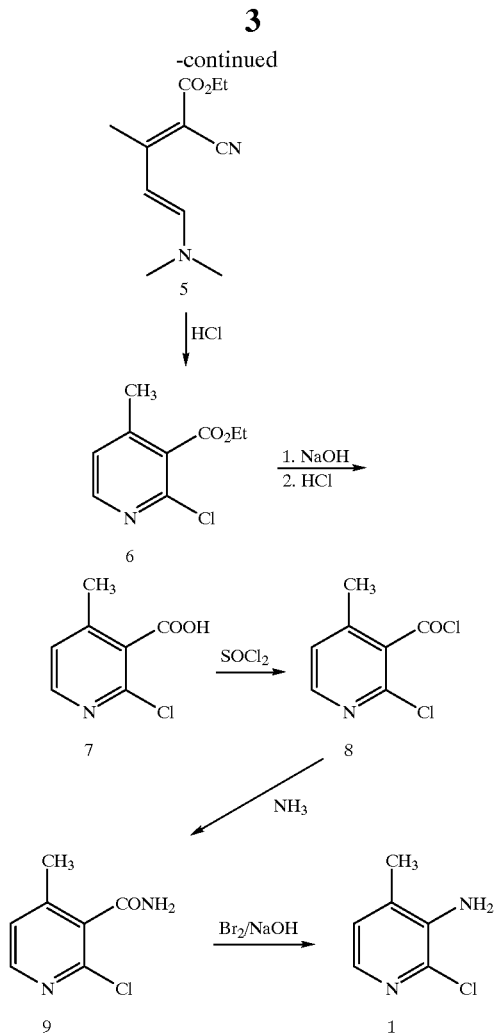

In accordance with the invention, and as shown in the reaction scheme shown above, the Knoevenagel reaction of acetone (2) with ethylcyanoacetate (3) gives ethylisopropylidenecyanoacetate (4). This is reacted with N.N-dimethylformamide dimethyl acetal to give the conjugated enamine (5). The enamine (5) is subjected to acid-catalyzed cyclization using HCl/EtOH, to give the ester (6), which is hydrolyzed to yield the acid (7). The acid (7) is converted to the acid chloride (8) by refluxing with an excess of thionyl chloride. The acid chloride (8) is then treated with anhydrous ammonia in ethanol, to yield 2-chloro-4-methyl-3-carboxamide (9). Finally, the amide (9) is converted via the Hofmann amide degradation reaction (treatment with solution of chlorine or bromine in excess sodium hydroxide by means of hypohalides), in a known per se manner, to the desired end product, 3-amino-2-chloro-4-methylpyridine (1).

DESCRIPTION OF THE PREFERRED EMBODIMENT

The following examples describe, in greater detail, the several steps of the process according to the invention and, together, represent the presently preferred embodiment of the invention.

EXAMPLE 1

Synthesis of ethyl isopropylidenecyanoacetate (4)

A mixture of 152 g (1.34 mole) of ethylcyanoacetate (3) in 152 g (2.62 mole) of acetone (2) containing 4 mL of piperidine was stirred at 20–30° C. for 16 hours then heated to reflux for 24 hours. Removing the volatile portion, the residue was distilled at 30–50$\mu$ of Hg. The fractions boiling at 56–67° C. were collected to give 169 g (82%) of a colorless oil.

B.P.: 91–92/1.5 mm Hg.

EXAMPLE 2

Synthesis of ethyl 2-cyano-5-(N,N-dimethylamino)-3-methyl-2,4-pentadienoate (5)

A mixture of 127.7 g (0.839 mole) of ethyl isopropylidenecyanoacetate (4) and 100 g (0.839 mole) of N.N-dimethylformamide dimethyl acetal in 500 mL of ethanol was refluxed for 24 hours. The ethanol was removed under reduced pressure to give 124 g (100%) of a dark oil.

MS: (MH)$^+$209, NMR (CDCl$_3$) ppm: 1.30 (t,3H); 2,3 (s,3H); 3.0 (s,3H); 3.2 (s,3H); 4.2 (q,2H); 7.1 (d,1H); 7.3 (d,1H)

EXAMPLE 3

Synthesis of ethyl 2-chloro-4-methylnicotinate (6)

Hydrogen chloride was introduced to a stirred mixture of 164 g (0.839 mole) of crude ethyl 2-cyano-5-(N,N-dimethylamino)-3-methyl-2,4-pentadienoate (5) in 500 mL ethanol at 20–45° C. The mixture was stirred at ambient temperature overnight, then heated to reflux for 8 hours. The ethanol was removed under reduced pressure and the residue distilled under high vacuum at 84–94° C., to give 47.7 g (30.4%) of a yellow oil, MH$^+$200, NMR (CDCl$_3$), ppm: 1.42 (t,3H); 2.36 (s,3H); 4.46 (q,2H); 7.12 (d,1H); 8.28 (d,1H).

Anal. Calcd.: C, 54.14; H, 5.05, N, 7.02; Cl, 17.76%;

Found: C, 54.19; H, 5.03, N, 7.10; Cl, 17.79%.

EXAMPLE 4

Synthesis of 2-chloro-4-methylnicotinic acid (7)

A mixture of 21.8 g (0.109 mole) of ethyl 2-chloro-4-methyl-nicotinate (6) and 55 mL of a 2N-sodium hydroxide solution in 20 mL of ethanol, was refluxed for 8 hours. The solution was acidified with 2N hydrochloric acid and extracted with ether. The organic phase was dried over magnesium sulfate, filtered and concentrated to give 14.8 g (79%) of 2-chloro-4-methylnicotinic acid (7)_as a white solid, mp: 152–154° C., MS (MH)$^+$172, NMR (DMSO) ppm: 2.34 (s,3H); 7.39 (d,1H); 8.33 (d,1H); 14.0 (bs COOH).

Anal. Calcd.: C, 49.00; H, 3.52; Cl, 21.22; N, 8.16%;

Found: C, 49.15; H, 3.56; Cl, 20.97; N, 8.00%.

EXAMPLE 5

Synthesis of 2-chloro-4-methylpyridine-3-carboxamide (9)

A mixture of 13.6 g (0.079 mole) of 2-chloro-4-methylnicotinic acid (7) and 100 mL of thionyl chloride was refluxed for 2 hours. The excess SOCl$_2$ was distilled off. The residue was dissolved in 100 mL of toluene, then concentrated under reduced pressure to remove all SOCl$_2$. The remaining acid chloride (8) was re-dissolved in 200 mL of toluene, cooled to 5° C. in an ice-bath. Ammonia gas was passed through the solution until a pH of 9 was obtained. The suspension was stirred at 20–25° C. for 12–16 hours, filtered and washed with toluene. The residue was suspended in methylene chloride/ethanol, filtered to remove $NH_4Cl$ and conc. to give 13 g (97.6%) mp: 178–180° C., $(MH)^+171$, NMR (DMSO) ppm:2.3 (s,3H), 7.33 (d,2H); 7.9 (d,$NH_2$); 8.2 (d,1H).

Anal. Calcd.: C, 49.28; H, 4.14; N, 16.42, Cl, 20.28%;
Found: C, 49.52, H, 4.11; N, 16.35, Cl, 20.91%.

EXAMPLE 6

Synthesis of 3-amino-2-chloro-4-methylpyridine (1)

A solution of 11.7 g (0.293 mole) of sodium hydroxide in 11 mL of water was stirred and cooled to 0° C. Bromine 14.2 g (0.293 mole) was added dropwise maintaining the temperature at 0° C. To a pale yellow solution was added 13.2 g (0.077 mole) of 2-chloro-4-methylpyridine-3-carboxamide (9) in portions at 0–5° C. The ice-bath was removed and the reaction mixture warmed to 75° C. over one hour and maintained at 60–75° C. for an additional 2 hours. The mixture was cooled overnight and the crystalline product collected by filtration to give 10 g (90.6%) of the title compound [mp: 62–64° C.]. NMR and MS was identical to data reported by Hargrave et al., *J. Heterocyclic Chem.*, 34, 223 (1991).

What is claimed is:

1. A method for making 3-amino-2-chloro-4-methylpyridine comprising the following steps:

(a) reacting ethylcyanoacetate with acetone to yield ethylisopropylidenecyanoacetate;

(b) reacting the ethylisopropylidenecyanoacetate so produced with N.N-dimethylformamide dimethyl acetal to yield ethyl 2-cyano-5-(N,N-dimethylamino)-3-methyl-2,4-pentadienoate;

(c) treating the ethyl 2-cyano-5-(N,N-dimethylamino)-3-methyl-2,4-pentadienoate so produced with hydrogen chloride in ethanol, to effect ring closure, thus producing ethyl 2-chloro-4-methylnicotinate;

(d) hydrolyzing the ethyl 2-chloro-4-methylnicotinate so produced to yield 2-chloro-4-methylnicotinic acid;

(e) reacting the 2-chloro-4-methylnicotinic acid so produced with thionyl chloride to yield the corresponding acid chloride;

(f) treating the acid chloride so produced with anhydrous ammonia in ethanol, to yield 2-chloro-4-methyl-3-carboxamide; and, (g) converting the 2-chloro-4-methyl-3-carboxamide so produced, via the Hofmann reaction (treatment with solution of chlorine or bromine in excess sodium hydroxide), to 3-amino-2-chloro-4-methylpyridine.

* * * * *